United States Patent
Mateus et al.

(10) Patent No.: US 11,246,321 B2
(45) Date of Patent: Feb. 15, 2022

(54) WHEY PROTEIN COMPOSITIONS AND METHODS

(71) Applicant: NESTEC S.A., Vevey (CH)

(72) Inventors: Marie-Louise Mateus, Le Mont-sur-Lausanne (CH); Pascaline Hoebler, Muntelier (CH); Nicolas Auriou, Bern (CH); Peter Fankhauser, Konolfingen (CH)

(73) Assignee: Societe des Produits Nestle S.A., Vevey (CH)

( * ) Notice: Subject to any disclaimer, the term of this patent is extended or adjusted under 35 U.S.C. 154(b) by 220 days.

(21) Appl. No.: 15/055,838

(22) Filed: Feb. 29, 2016

(65) Prior Publication Data

US 2016/0174588 A1   Jun. 23, 2016

Related U.S. Application Data

(62) Division of application No. 13/124,390, filed as application No. PCT/EP2009/007454 on Oct. 16, 2009, now abandoned.

(60) Provisional application No. 61/106,384, filed on Oct. 17, 2008.

(51) Int. Cl.
| | | |
|---|---|---|
| *A23C 21/08* | (2006.01) | |
| *A23C 21/04* | (2006.01) | |
| *A23C 21/06* | (2006.01) | |
| *A23L 33/00* | (2016.01) | |
| *A23L 33/19* | (2016.01) | |
| *A23C 21/10* | (2006.01) | |

(52) U.S. Cl.
CPC ........... *A23C 21/08* (2013.01); *A23C 21/04* (2013.01); *A23C 21/06* (2013.01); *A23C 21/10* (2013.01); *A23L 33/19* (2016.08); *A23L 33/30* (2016.08); *A23L 33/40* (2016.08); *A23V 2002/00* (2013.01)

(58) Field of Classification Search
None
See application file for complete search history.

(56) References Cited

U.S. PATENT DOCUMENTS

| | | |
|---|---|---|
| 5,520,948 A | 5/1996 | Kvamme |
| 5,549,905 A | 8/1996 | Mark et al. |
| 5,641,531 A | 6/1997 | Liebrecht et al. |
| | (Continued) | |

FOREIGN PATENT DOCUMENTS

| | | |
|---|---|---|
| EP | 0486425 | 5/1992 |
| EP | 1314361 | 5/2003 |
| | (Continued) | |

OTHER PUBLICATIONS

Gonzalez-Tello et al. "Density, Viscosity and Surface Tension of Whey Protein Concentrate Solutions" Journal of Food Process Engineering, 2009, vol. 32, pp. 235-247.

(Continued)

*Primary Examiner* — Jenna A Watts
(74) *Attorney, Agent, or Firm* — K&L Gates LLP

(57) ABSTRACT

The present invention provides various whey protein compositions as nutritional formulations suitable for use as ready-to-use liquid compositions that are shelf-stable and contains high level of intact whey protein content. The present invention further provides the methods of making such compositions.

11 Claims, 4 Drawing Sheets

(56) References Cited

U.S. PATENT DOCUMENTS

| | | | |
|---|---|---|---|
| 6,093,425 A * | 7/2000 | Kamarei | A23C 9/1322 229/125.42 |
| 6,106,874 A * | 8/2000 | Liebrecht | A23L 2/02 426/583 |
| 7,247,320 B2 | 7/2007 | Jost | |
| 2003/0099761 A1† | 5/2003 | Jost | |
| 2010/0196559 A1 | 8/2010 | Smulders et al. | |

FOREIGN PATENT DOCUMENTS

| | | | |
|---|---|---|---|
| EP | 1314361 | A1 | 5/2003 |
| EP | 1839492 | | 10/2007 |
| JP | 63-109737 | A | 5/1988 |
| JP | 04-267864 | | 9/1992 |
| JP | 07-099885 | | 4/1995 |
| JP | 07-264980 | | 10/1995 |
| JP | 08-056568 | | 3/1996 |
| JP | 08-196236 | | 8/1996 |
| JP | 2002-538797 | | 11/2002 |
| JP | 2003-520754 | | 7/2003 |
| JP | 2004-506463 | | 3/2004 |
| JP | 2007-532534 | | 11/2007 |
| JP | 2007-535940 | | 12/2007 |
| JP | 2009-531038 | | 9/2009 |
| JP | 2009-9248133 | A | 10/2009 |
| WO | 97/11614 | | 4/1997 |
| WO | 9942001 | | 8/1999 |
| WO | 99/56563 | | 11/1999 |
| WO | 02/15719 | A2 | 2/2002 |
| WO | 0215720 | | 2/2002 |
| WO | 2005096845 | | 10/2005 |
| WO | 2007/108827 | A1 | 9/2007 |
| WO | 2007108827 | A1 † | 9/2007 |
| WO | 2007/110411 | A2 | 10/2007 |
| WO | 2007/110421 | A2 | 10/2007 |
| WO | 2007/110422 | A2 | 10/2007 |
| WO | 2007/110423 | A2 | 10/2007 |
| WO | 2007110421 | A2 † | 10/2007 |
| WO | 2008/135960 | A2 | 11/2008 |
| WO | 2009011573 | A1 † | 1/2009 |
| WO | 2009/038746 | A1 | 3/2009 |
| WO | 2009038746 | A1 † | 3/2009 |
| WO | 2009072884 | | 6/2009 |
| WO | 2009113845 | | 9/2009 |
| WO | 2009113858 | A1 † | 9/2009 |

OTHER PUBLICATIONS

Bounous et al., "Whey proteins as a food supplement in HIV-seropositive individuals", Clin. Invest. Med., 1992, pp. 204-209, vol. 16, No. 3.

Castellanos et al., "Modular Protein Supplements and Their Application to Long-Term Care", Nutrition in Clinical Practice, Oct. 2006, pp. 485-504, vol. 21.

Combaret et al., "A leucine-supplemented diet restores the defective postprandial inhibition of proteasome-dependent proteolysis in aged rat skeletal muscle", J. Physiol., 2005, pp. 489-499, vol. 2.

Dardevet et al., "Stimulation of In Vitro Rat Muscle Protein Synthesis by Leucine Decreases with Age", The Journal of Nutrition, 2000, pp. 2630-2635.

Dardevet et al., "Leucine: a key amino in ageing-associated sarcopenia?", Nutrition Research Reviews, 2003, pp. 61-70, vol. 16.

De Wit et al., "Functional Properties of Whey Proteins", pp. 285-321.

Kanno, "Purification and Separation of Multiple Forms of Lactophorin from Bovine Milk Whey and Their Immunological and Electrophoretic Properties", J. Dairy Science, 1989, pp. 883-891, vol. 72.

Layman et al., "Dietary Impact on Glycemic Control during Weight Loss", The Journal of Nutrition, 2004, pp. 968S-973S.

Micke et al., "Oral supplementation with whey proteins increases plasma glutathione levels of HIV-infected patients", European Journal of Clinical Investigation, 2001, pp. 171-788, vol. 31.

Morr et al., "Composition and Functionality of Commercial Whey and Milk Protein Concentrates and Isolates: A Status Report", Food Technology, Apr. 1990, pp. 100-110.

Morr et al., "Whey Protein Concentrates and Isolates: Processing and Functional Properties", Food Science and Nutrition, 1993, pp. 431-476, vol. 33, No. 6.

Salimen eta1., "Probiotics: how should they be defined?", Trends in Food Science & Technology, 1999, pp. 107-110, vol. 10.

Reiter, "The Biological Significance of Lactoferrin", Int. J. Tiss. Reac., 1983, pp. 87-96, vol. 1.

International Seach Report and Written Opinion dated Nov. 10, 2010 for related Intl. Appln. PCT/EP2009/007454.

"Milk" Wikipedia, The Free Encyclopedia, http://en.wikipedia.org/wiki/Milk, dated Jul. 17, 2014.

European Office Action for Application No. 09755838.1 dated Jul. 29, 2014, 7 pages.

\* cited by examiner
† cited by third party

WHEY PROTEIN COMPOSITIONS AND METHODS

PRIORITY CLAIM

The present application is a division of U.S. patent application Ser. No. 13/124,390, filed on Jun. 30, 2011, which is a National Stage of International Application No. PCT/EP09/07454, filed on Oct. 16, 2009, which claims the benefit of U.S. Provisional Patent Application No. 61/106,384, filed on Oct. 17, 2008, the entire contents of each of which are being incorporated herein by reference.

FIELD OF TECHNOLOGY

The present invention relates to shelf-stable, acid and neutral whey compositions, having high level of protein content for a nutritional supplement or beverage, methods of production of these compositions and uses of such compositions in the manufacture of a functional food or as a nutritional supplement during illnesses and prior to and after surgery. The present invention further relates to nutritional compositions that are not only useful and applicable for medical purposes but also for sports and health fitness enthusiasts.

BACKGROUND

Nutritional supplements or beverages have been developed to assist people who do not take in sufficient nutrients for nutritional complete diet. Nutritional supplements are provided to people who are ill due to an illness, convalescing from surgery or anti-cancer therapy, anorexic, and elderly. They are also beneficial and useful to serious athletes and proactive health seekers. Various forms of nutritional supplements are commercially available and the protein sources for these supplements are either as caseinates and soy protein isolates or a combination of casein and whey protein sources.

The level of the protein source in the commercial liquid formulation products, as reviewed, are attributed to casein in form of Ca-, Na- or K-caseinate or from milk protein concentrate (MPC). Nutritional supplements that are based on other proteins such as whey protein are also available. In fact, some shelf-stable liquid formulations based on intact whey protein are commercially-available, e.g., Novartis' Resource® and Clinutren Fruit®.

To provide an ideal nutritional supplement that offers as many beneficial and health benefits to sick, convalescing and anorexic patients or elderly people treatment, it is important to use a superior and at the same time, good quality protein that has the highest biological value (BV-100%). The Food and Agricultural Organization/World Health Organization proposed a superior mean to identify protein quality, called "protein digestibility corrected amino acid score (PDCAAS)," which indicates how well a particular protein provides the required essential amino acids. When assessed, egg and milk proteins (whey protein and casein) appear to be the best quality proteins, as indicated by their net protein utilization (NPU; nitrogen retained in body/nitrogen consumed), biological value (BV; nitrogen retained in body/nitrogen absorbed by gut); and protein efficiency ratio (PER; weight gain/nitrogen consumed). Among the milk proteins, however, whey has the highest scores and proves to be of superior quality, as illustrated hereinbelow. See Castellanos, D. et al., Nutr. Clin. Practice, 21:485-504 (2006).

Protein Quality Comparison Chart

| Reference Proteins | Protein Digestibility Corrected Amino Acid Score (PDCAAS)[i] | Amino Acid (AA) Score | Protein Efficiency Ratio (PER)[ii] | Biological Value (BV) | Protein Digestibility % (PD) |
|---|---|---|---|---|---|
| Whey Protein Concentrate | 1.0 | 1.14 | 3.2 | 104 | 99 |
| Whole Egg | 1.0 | 1.21 | 3.8 | 100 | 98 |
| Casein | 1.0 | 1.19 | 2.9 | 77 | 99 |
| Soy Protein Concentrate | 0.99 | 1.04 | 2.2 | 74 | 95 |
| Beef | 0.92 | 0.94 | 2.9 | 80 | 98 |
| Wheat gluten | 0.25 | 0.47 | 0.34 | 54 | 91 |

[i]Protein Quality Evaluation, Report of the Joint FAO/WHO Consultation 1991
[ii]Reference Manual for U.S. Whey Products, 2nd Edition, U.S. Dairy Export Council, 1999

The pronounced heat lability of whey protein in sterilizing heat treatments poses as a problem, which is not experienced when casein is used as a protein source. Heat treatment by way of sterilization or pasteurization is required for bacterial safety during non-refrigerated storage. However, high temperatures required for sterilization lead to denaturation of whey proteins followed by aggregation and gelling. As a result, liquid, shelf-stable formulations with native whey proteins are scarce or contain relatively low amounts of whey proteins that are typically lower than 8%.

In consideration of the high nutritional protein quality of whey protein, the use of this protein source in enteral nutritional formulation appears to be very desirable. Due to heat-induced gelling or sedimentation, however, it has not been possible so far to incorporate into such formulation a markedly higher concentration of whey protein than what is present in commercial milk protein concentrates (in milk protein concentrate, whey proteins constitute about 20% of the total protein).

A known solution to this stability problem is the partial hydrolysis of whey protein by proteases, prior to the introduction of the material into a composition that is subjected to sterilizing heat treatments.

An example of a commercial enteral formula containing 40 g/l of partially-hydrolyzed whey protein is PEPTAMEN®, the protein of which has been partially-hydrolysed by trypsin and thereby rendered stable to sterilizing heat treatment. It is also possible to combine whey protein hydrolysates with casein hydrolysates or caseinates to make up the protein basis of a formula. An example of such an approach is disclosed in U.S. Pat. No. 5,821,217 (describing an enteral formula containing protein hydrolysates) or in U.S. Pat. No. 5,549,905 (describing a pediatric patient's formula containing 12% of the calories in form of hydrolysed whey protein).

The use of partially-hydrolysed (whey) protein may be a possible approach; however, an inherent disadvantage of such use is the bitter taste resulting from the incorporation of partially hydrolysed protein into such formulations. While bitter taste is not a significant problem in a tube feeding mode, it becomes a serious problem in a formula intended for oral consumption.

To produce a bland tasting whey protein-based enteral formulation with long non-refrigerated shelf life, approaches other than hydrolysis must be found to stabilize the protein or else the formula will not be palatable.

Two recent developments seem to go in this direction, but they do not achieve the goal of sterility and long shelf life which exploits the known acid stability of whey protein. EP 0 486 425 describes the production of a whey protein-based formula (at least 60% whey protein) having a pH between 3.5 and 3.9 and a whey protein content of about 3.88% (9.81 g in 237 ml). The low pH of the formula was obtained by the addition of citric and phosphoric acid. The formula received a pasteurizing heat treatment: at 95.6° C. for 4.3 seconds. In International Patent Publication No. WO 99/56563 (corresponding to U.S. Pat. No. 6,475,539), a low pH (pH 3.0-4.6) enteral formula is described, wherein a highly methoxylated pectin (0.6-1.25%) is used as a protein stabilizer. The amount of whey protein concentrate employed in the acid beverage formula, as described ranges from 0.70 g/100 g to 0.75 g/100 g. Whey proteins added to the acid beverage formula can be in form of whey protein concentrate, whey protein isolates or partially hydrolysed whey protein. A particular variant of this formula contains intact whey protein as a protein source; the final pH of the formula is 4.0-4.35 and the heat treatment applied to the formula is 102-104° C. for 18 seconds.

Based on the above discussion, there is a need to produce a commercially-sterile, shelf-stable whey liquid composition, either in form of an acid or a neutral liquid formulation, wherein all or major portion of the protein content, i.e., ranging from above 60% to 100%, is composed of intact (unhydrolysed) whey protein. In addition, there is also a need to produce a shelf-stable, oral and drinkable liquid whey protein products that possess appealing organoleptic properties (good texture and sensorial taste, e.g., smooth and creamy with a pleasant taste without sandiness and bitter mouth taste). Furthermore, there is a long-felt need to produce a commercially-sterile, shelf-stable whey liquid composition that contains a superior and good quality "fast" protein such as whey that can provide numerous health benefits to the patients in need of such treatment.

The methods and means of accomplishing each of the above needs, as well as others, will become apparent from the detailed description.

SUMMARY

The present invention provides various shelf-stable whey liquid or gel compositions having high protein content and methods for preparing such compositions.

To this end, the present invention provides shelf-stable, acid whey compositions having high whey protein content and a pH ranging between 3.5 to 4.3 that are beneficial and applicable for various purposes. The shelf-stable, acid whey compositions, according to the present invention, either in liquid or in gel form, may have (1) a total whey protein content ranging from about 9 g/100 g to about 13.5 g/100 g, based on the total weight of the compositions and which provides a total energy intake ranging from about 14-54%; and (2) a total energy content ranging from at least about 100-264 kcal/100 g. In addition, the shelf-stable, acid whey compositions may include at least one macronutrients, e.g., at least one carbohydrate source and/or a fat or lipid source. The fat or lipid source may range from at least about 0-12 g/100 g (0-12%) based on the total weight of the compositions and which provides at least about 0-41% of the total energy intake. For example, the fat source may range from at least about 0, 0.25, 0.5, 0.7, 0.9, 1, 2, 3, 4, 5, 6, 7, 8, 9, 10, 11 or 12 g/100 g based on the total weight of the composition, which, in turn, may provide a total energy content of at least about 0%; 0.5%, 0.7%, 1.0%, 2.5%, 5%, 10%, 15%, 20%, 25%, 30%, 32%, 35%, 37%, 39%, 40% or 41%. In one embodiment, the fat source in one of the acid whey compositions may be 0%.

The carbohydrate source may range from at least about 12-55 g/100 g based on the total weight of the compositions. For example, the carbohydrate source may provide at least about 12-20, 12-26; 15-30; 15-55 g/100 g, based on the total weigh of the compositions, which, in turn, provides, at least about 39-85% of the total energy intake. For example, carbohydrate source in the acid whey compositions may provide an energy content ranging from at least about 39%-46%, 45%-64%, 51%-70%, 57%-76%, or 60%-85%.

The shelf-stable, acid whey compositions, as described hereinbelow, may be in form of a liquid or a gel depending on the amount of the total whey protein content and total energy content contained in the compositions.

The compositions of the present invention may provide a protein content of at least about 8 g/100 g to 13.5 g/100 g, wherein the total protein content is composed of at least about 60 to at least about 100% whey protein. For example, the total protein content may compose of at least about 65%, 70%, 75%, 80%, 85%, 90%, 95% or 100% whey protein. Preferably, the total protein content may range from at least about 80-100%; 85-100%, 90%¬100% or at least about 95%-100% whey protein. More preferably, the total protein content may compose of at least about 95%, 96%, 97%, 98%, 99% or 100% whey protein.

Whey protein may be unhydrolyzed or hydrolyzed whey protein. The protein content may be at least about 8 g/100 g; 8.5 g/100 g; 9 g/100 g; 9.5 g/100 g; 10 g/100 g; 10.5 g/100 g; 11 g/100 g; 11.5 g/100 g; 12 g/100 g; 12.5 g/100 g; 13 g/100 g; or 13.5 g/100 g of whey protein, either in form of whey protein concentrate; whey protein isolates, whey protein micelles and whey protein hydrolysates or in any combination thereof. The whey protein content may range from at least about 8 g/100 g or at least about 13.5 g/100 g.

In one embodiment, the present invention provides shelf-stable, acid whey compositions having an energy content of at least about 100-264 kcal/100 g and a protein content of at least about 13.5 g/100 g, wherein the total protein content is composed of at least about 90%-100% whey protein, either in unhydrolyzed or hydrolyzed intact forms. The pH range of this composition at ambient temperature, according to the invention, may be at least about 3.5 to about 4.3. The pH range may also be at least about 3.9 to about 4.1. In this composition, the total protein content may compose of at least about 90%-100%, at least about 95%-100%, at least about 95% or at least about 100% whey protein, all of which can be in form of (1) native whey, e.g., whey protein micelles, whey protein concentrate and whey protein isolates; and (2) whey protein hydrolysates. The compositions of the invention have organoleptic properties, i.e., smooth and creamy texture. The compositions may provide an energy content ranging from at least about 100 kcal/100 g to 264 kcal/100 g. For example, at least about 100-120, 120-130, 130¬140, 140-150, 150-160, 160-180, 180-200, 200-220, 220-240, 240-264 kcal/100 g, preferably at least about 185 kcal/100 g or about 260 kcal/100 g. In addition, the ratio of whey protein micelles or whey protein concentrate or whey protein isolates to whey protein hydrolysates in the composition may range from at least about 40:60 to 100:0; 40:60 to 60:40; 50:50 to 80:20, preferably at a ratio of at least about 70:30.

The shelf-stable, acid whey liquid compositions having an energy content ranging from at least about 100 kcal/100 g to about 264 kcal/100 g and a protein content of at least about 13.5 g/100 g, according to the present invention, provide (1) a protein source having an overall total energy intake of at least about 20-54%; (2) a fat source of at least about 0-12 g/100 g based on the total weight of the composition, which provides at least about 0-41% of the total energy intake; and (3) at least one carbohydrate source of at least about 12-26 g/100 g, based on the total weight of the composition, which provides at least about 39-46% of the total energy intake.

In another embodiment, the present invention further provides a shelf-stable, acid whey compositions that provide at least about 100 kcal/100 g to at least about 264 kcal/100 g of total energy content, a pH range of at least about 3.5 to about 4.3, and a whey protein content of at least about 9 g/100 g. The total protein content in this composition may compose of at least about 90%-100%, at least about 95%-100%, at least about 95% or at least about 100% whey protein. Such compositions as described herein, may provide an energy content ranging from at least about 100 kcal/100 g to 264 kcal/100 g. For example, at least about 100-120, 120-130, 130-140, 140-150, 150-160, 160-180, 180-200, 200-220, 220-240, 240-264 kcal/100 g, preferably at least about 185 kcal/100 g or at least about 260 kcal/100 g. In addition, the ratio of whey protein isolates or whey protein concentrate or whey protein micelles to whey protein hydrolysates in such compositions may range from at least about 40:60 to 100:0; 40:60 to 60:40; 50:50 to 80:20, preferably at a ratio of at least about 70:30.

The shelf-stable, acid whey composition having an energy content of at least about 100 kcal/100 g to about 264 kcal/100 g and a protein content of at least about 9 g/100 g provides an overall total energy intake from the protein source of at least about 14-36%; at least one fat source of at least about 0-12 g/100 g, based on the total weight of the composition, which provides at least about 0-41% of the total energy intake; and at least one carbohydrate source of at least about 16-30 g/100 g, based on the total weight of the composition, which provides at least about 45-64% of the total energy intake.

For a shelf-stable, acid compositions having a total whey protein content of at least about 10 g/100 g and a total energy content ranging from at least about 100 kcal/100 g to about 260 kcal/100 g, the ratio of whey protein isolates or whey protein concentrate or whey protein micelles to whey protein hydrolysates ranges from at least about 40:60 to 100:0; 40:60 to 60:40; 50:50 to 80:20, preferably at a ratio of at least about 60:40. The total energy intake provided by the protein source is at least about 15-40%. The amount of carbohydrate source in such compositions is at least about 15-55 g/100 g, based on the total weight of the compositions, which provides at least about 60-85% of the total energy intake. The fat or lipid source may be 0%.

To arrive at the above-mentioned shelf-stable, acid whey compositions, either in liquid or gel form, the present invention also provides several methods for producing the various shelf-stable, acid whey compositions having a total whey protein content ranging from at least about 9-13.5 g/100 g and a total energy content that ranges from at least about 100-264 kcal/100 g.

In one embodiment, the present invention provides a method for producing shelf-stable, acid whey compositions having a whey protein content of at least about 9-13.5 g/100 g, wherein the total protein content is composed of at least about 90%-100% whey protein and an energy content that ranges from at least about 100-260 kcal/100 g, and wherein the methods comprises:

(a) admixing water, at least one emulsifier and at least one whey protein having a total energy intake of at least about 14-54%, to form a first mixture at a temperature range of at least about 30-55° C. for about 10 min;

(b) admixing to the first mixture at least one carbohydrate source of at least about 12-30% and at least one fat source of at least about 0-12% to form a second mixture;

(c) adjusting the pH of the second mixture to at least about 3.5 to 4.3 by adding a food grade acid or an alkali solution to obtain an acid whey mixture;

(d) preheating the acid whey mixture at a temperature range of about 60-80° C. for about 1-10 seconds, (e) heating the acid whey mixture at a temperature range of about 120° C. for about 11 seconds under direct steam injection, followed by a flash at a temperature of about 60-80° C. to obtain a shelf-stable, acid whey composition;

(f) homogenizing the shelf-stable, acid whey composition at 100-240 bar pressure;

(g) optionally, cooling the shelf-stable, acid whey composition at a temperature range of about 20° C. to 30° C.; and (h) transferring the shelf-stable, acid whey composition into a sterile container.

In yet another embodiment, a shelf-stable, acid whey composition is provided, which has a protein content from at least about 9 g/100 g to at least about 13.5 g/100 g produced by the method, as described hereinabove.

In yet another embodiment, a shelf-stable, acid whey composition is provided, which has an energy content ranging from at least about 100 kcal/100 g to about 260 kcal/100 g and a protein content of at least about 10 g/100 g, wherein the total protein content is composed of at least about 90-100% whey protein. The whey protein, as used herein, may be in form of unhydrolysed or hydrolysed intact whey protein. The whey protein source may be from native whey, e.g., whey protein micelles, whey protein concentrate or whey protein isolates, and whey protein hydrolysates. Similar to the above-mentioned compositions, the shelf-stable, acid whey liquid compositions possess acceptable organoleptic properties and have an energy content that ranges from at least about 100 kcal/100 g to at least about 260 kcal/100 g, for example, at least about 100-120, 120-130, 130-140, 140-150, 150-160, 160-180, 180-200, 200-220, 220-240, 240-264 kcal/100 g. In addition, the ratio of whey protein isolates to whey protein hydrolysates in such compositions may range from at least about 40:60 to 100:0; 40:60 to 60:40; 50:50 to 80:20, preferably at a ratio of at least about 70:30. The whey protein source in the composition provides at least about 15-40% of the total energy intake. There is no available fat or lipid source, however, with respect to the carbohydrate source, there is at least about 15-55 g/100 g of the total weight of the composition, which provides about 60-85% of the total energy intake. The pH of the composition at ambient temperature, according to the invention, is between 3.5 and 4.3. In one embodiment, the pH of the acid whey composition as described herein, may range from at least about 3.9 to 4.1.

To prepare shelf-stable, acid whey compositions having a total whey protein content of at least about 10 g/100 g, based on the total weight of the composition and an energy content that ranges from at least about 100 kcal/100 g to about 260 kcal/100 g and a pH range of at least about 3.5-4.3, preferably between 3.9 to 4.1. The present invention also provides a method to prepare such compositions that comprises:

(a) admixing water with at least one emulsifier and at least one whey protein having a total energy intake of at least about 15-40%, to form a first mixture at a temperature range of at least about 30-55° C. preferably at about 50° C., for about 10 min;

(b) admixing to the first mixture at least one carbohydrate source of about 15-55% to form a second mixture;

(c) adjusting the pH of the second mixture to at least about 3.5 to 4.3 by adding a food grade acid or an alkali solution to obtain an acid whey mixture;

(d) preheating the acid whey mixture at a temperature range of about 60-80° C. for about 1-10 seconds, (e) heating the acid whey mixture at a temperature range of about 90° C. for about 11-15 seconds under direct steam injection, followed by a flash at a temperature of about 60-80° C. to obtain a shelf-stable, acid whey composition;

(f) homogenizing the shelf-stable, acid whey composition at 100-240 bar pressure;

(g) transferring the shelf-stable, acid whey composition into a sterile container; and (h) cooling the shelf-stable, acid whey composition at a temperature range of about 20° C. to 30° C.

In one embodiment, the present invention provides a shelf-stable, acid whey liquid composition having an energy content that ranges at least about 100-260 kcal/100 g and a protein content of about 10 g/100 g produced by the method as discussed above.

In another embodiment, at least one additional ingredient may employed by the methods, as described elsewhere in this patent application may be selected from the group consisting of a vitamin, a trace mineral, a trace element, a buffering agent, a thickening agent, a sweetener, a flavoring agent, a colorant, a fiber, a starch, a prebiotic, an amino acid, a nucleoside and an herbal agent, and extracts from fruits & vegetables.

In a further embodiment, the present invention provides a neutral, shelf-stable and enteral non-gel liquid composition having a protein content ranging from at least about 8 g/100 g to at least about 13.5 g/100 g or from at least about 90 g/L to at least about 143 g/L, wherein the total protein content is composed of at least about 60-100% unhydrolysed intact whey. In one embodiment, the total protein content may compose of at least about 90%-100%; at least about 95%-100%; at least about 95% or at least about 100% unhydrolysed intact whey.

In another embodiment, the whey protein source is from unhydrolysed whey, for example, whey protein concentrate, whey protein micelles or whey protein isolates and from whey protein hydrolysates. The whey protein source can also be a combination of whey protein concentrate and whey protein isolates or whey protein hydrolysates. In yet another embodiment, the whey protein source may composed of 100% whey protein concentrate or 100% whey protein micelles, wherein the total protein content ranges from at least about 8 g/100 g to about 10 g/100 g (for whey protein concentrate) or at least from about 8 g/100 to about 13 g/100 g (for whey protein micelles), respectively. The whey protein micelles may be in liquid or powdered form.

An advantage of the present invention is that the composition has a pH ranging from at least about 6.5-7.5 and may be lactose-free. It may further comprise leucine, cysteine, or an amino acid. The composition may be used for oral supplementation, tube feeding or enteral administration.

Another advantage of the present invention is that the composition possesses good textural and sensorial properties and has a viscosity that is below 200 mPas at a temperature of at least less than or equal to 20° C.

Yet another advantage of the neutral, shelf-stable and enteral non-gel liquid composition according to the present invention may have an energy content ranging from at least about 110 kcal/100 g to at least about 200 kcal/100 g. For example, at least about 110¬120 kcal/100 g, 110-130 kcal/100 g, 110-140 kcal/100 g, 120-140 kcal/100 g, 140-160 kcal/100 g, 160-180 or 180-200 kcal/100 g; at least above 140 kcal/100 g or at least above 180 kcal/100 g, preferably an energy content ranging from at least about 140 to 160 kcal/100 g. In one embodiment, the neutral, shelf-stable and enteral non-gel liquid composition may have an energy content that is at least above 140 kcal/100 g.

A further advantage of the present invention is that the neutral, shelf-stable and enteral non-gel liquid further comprises at least one additional ingredient that is selected from the group consisting of at least one carbohydrate source, lipid source, vitamin, a mineral, a trace element, a buffering agent, a thickening agent, a sweetener, a flavoring agent, a colorant, a fiber, a starch, a prebiotic, an amino acid, a nucleoside, an herbal agent and extracts from fruit and vegetables. The vitamin, mineral, and trace element are all used in amounts according to the FSMP regulations.

In another embodiment, at least one carbohydrate source is maltodextrin and/or sucrose and lactose and ranges from about 10 g to about 20 g/100 g, based on the total weight of the composition. In addition, at least one lipid source is selected from the group consisting of corn oil, rapeseed oil, and soybean oil, wherein at least one lipid source is from at least about 0¬10 g/100 g or at least about 4-10 g/100 g, based on the total weight of the neutral, shelf-stable and enteral non-gel liquid composition.

In yet another embodiment, at least one thickening agent is selected from the group consisting of starch and carageenans.

The present invention provides a method for producing a neutral, shelf-stable and enteral non-gel liquid composition having an energy content that ranges from at least about 110 kcal/100 g to at least about 200 kcal/100 g and a total protein content that ranges from at least about 8 g/100 g to at least about 13 g/100 g or from at least about 90 g/L to at least about 143 g/L, wherein the method comprises:

(a) admixing at least one whey protein source with at least one carbohydrate source, lipid source and emulsifier in water at a temperature range of between 30 to 60° C., preferably 35° C., to form a first mixture;

(b) adding to the first mixture at least one mineral, vitamin, trace element, and thickening agent (e.g., starch) and at least one additional ingredient to form a second mixture;

(c) adjusting the pH of the second mixture to at least about 6.5 and 7.5, by adding a food grade acid (e.g., citric acid or phosphoric acid) or base (potassium hydroxide or sodium hydroxide) to obtain a neutral liquid composition that does not gel;

(d) preheating the neutral non-gel liquid composition at a temperature of between 60 and 80° C., preferably 65° C. (by means of a tubular heat exchanger);

(e) exposing neutral non-gel liquid composition under ultra-high temperature treatment using direct-steam injection (can be proceeded by a flash at a temperature range of between 60-65° C., preferably at about 65° C.) at a temperature range of between 140-145° C., preferably 145° C., for 7 seconds holding time to obtain a neutral, shelf-stable non-gel liquid composition;

(f) homogenizing the neutral, shelf-stable non-gel liquid composition at a temperature range of between 60-80° C., preferably at about 65° C., at a total pressure of 200 bars;

(g) cooling the neutral, shelf-stable non-gel liquid composition at a temperature range of about 20° C.-35° C.; and (h) transferring the neutral, shelf-stable non-gel liquid composition into a sterilized container for enteral use.

In an embodiment, the above-mentioned method further comprises aseptically adding lactase to the neutral, shelf-stable and enteral non-gel liquid composition if the composition is not lactose-free.

In another embodiment, a neutral, shelf-stable and enteral non-gel liquid composition has a protein content ranging from at least about 8 g/100 g to at least about 13 g/100 g or from at least about 90 g/L to at least about 143 g/L is produced according to the method as provided above.

A further advantage of the present invention is to provide a neutral, shelf-stable and enteral non-gel liquid composition having protein content ranging from at least about 8 g/100 g to at least about 13 g/100 g or from at least about 90 g/L to at least about 143 g/L, a pH ranging from at least about 6.5 to about 7.5, and an energy content ranging from at least about 110 kcal/100 g to at least about 200 kcal/100 g, wherein the total protein content is composed of at least about 60% to at least about 100% unhydrolysed intact whey.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

The terms "a" and "an," when used in conjunction with the word "comprising" in the claims or specification, denotes one or more, unless specifically noted.

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

As used herein, the term "comprise" and variations of the term, such as "comprising," "comprises" and "comprised," are not intended to exclude other additives, components, integers or steps.

As used herein, the term mammal includes but is not limited to rodents, aquatic mammals, domestic animals such as dogs and cats, farm animals such as sheep, pigs, cows and horses, and humans. Wherein the term mammal is used, it is contemplated that it also applies to other animals that are capable of the effect exhibited or intended to be exhibited by the mammal.

Any reference to a numerical range in this application should be construed as an express disclosure of every number specifically contained within that range and of every subset of numbers contained within that range. Further, this range should be construed as providing support for a claim directed to any number, or subset of numbers in that range. For example, a disclosure of 1-10 should be construed as supporting a range of 2-8, 3-7, 5, 6, 1-9, 3.6-4.6, 3.5-9.9, 1.1-9.9, etc.

DETAILED DESCRIPTION

Figure 1:
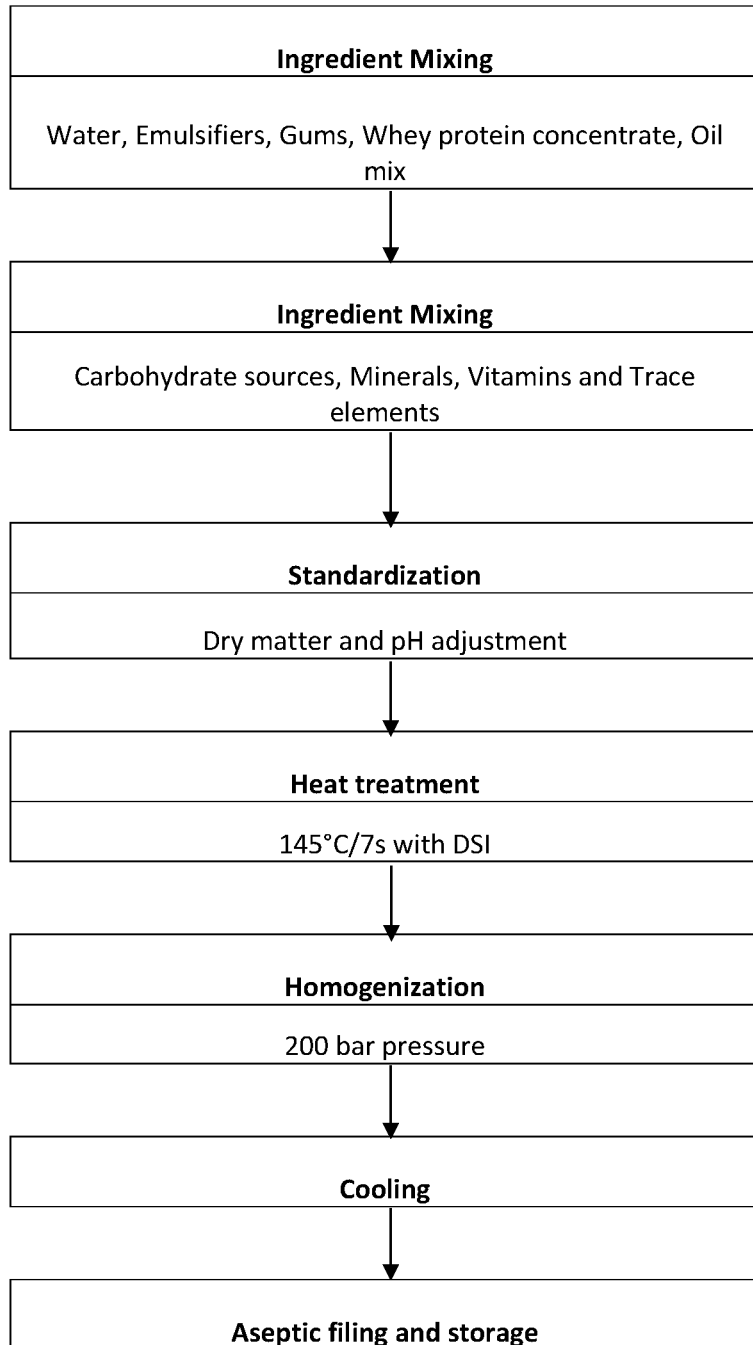
FIG. 1 is a flow diagram of how a shelf-stable, neutral whey liquid non-gel composition having up to 100% whey protein content (up to 10 g/100 g or 11 g/100 ml) was prepared.

The present invention concerns whey compositions having high protein content and methods of preparing such whey compositions, wherein all or major of the protein content is composed of 60-100%, preferably 100%, whey protein source. These whey compositions are in form of an acid or neutral liquid formulations.

In one embodiment, the pH of the shelf-stable acid whey liquid compositions, according to the present invention at ambient temperature, either having a low or high energy content, according to the invention, can be between 3.5 and 4.3, preferably between 3.9 to 4.1. In yet another embodiment, the pH of the aseptic, shelf-stable non-gel neutral whey liquid composition is in the range of about 6.5 to 7.5, preferably between 6.8 to 7.2.

Milk proteins contain two major constituents, namely, casein and whey proteins. Whey protein is the curd-free portion of milk that is left over from the production of cheese. Whey proteins are an excellent source of essential amino acids (EAA; 45%) that provide enhanced health benefits in comparison to casein or soy proteins. With respect to branched-chain amino acids (BCAAs), whey protein contains a relatively high level of BCAAs (☐26% including leucine, isoleucine and valine) with .apprxeq. 11-14% leucine. Layman D. K. et al., J. Nutr., 134:968S-973S (2004).

Whey is a "fast protein" and contains the highest amount of leucine, which helps maintain lean body mass. Besides its ability to enhance muscle development and building, as well as muscle maintenance in children, adults or elderly people, whey can stimulate the immune function, improve cognitive function, control blood glucose such that they are suitable for diabetics, weight management and satiety, anti-inflammatory effects, wound healing and skin repair, and lower blood pressure, etc. In view of these functional roles, whey protein-based supplements may mitigate sarcopenia, which is partly due to resistance of protein anabolism to plasma amino acid in the elderly. As reported, leucine is the key amino acid for the elderly in decreasing post-prandial muscle protein breakdown. See Dardevet, D. et al., Nutr. Res. Rev., 16:61-70, 2003; Combaret, L. et al., J. Physiol., 569 (Pt 2):489-99 (2005). Nutr. 2000 November; 130 (11): 2630-5.

When comparing whey to casein (containing 0.3 g cysteine/100 g protein), sweet whey proteins contain 7 times more cysteine while acid whey has 10 times more cysteine. Cysteine is the rate-limiting amino acid for glutathione (GSH) synthesis, a tripeptide made of glutamate cysteine and glycine which has primary important functions in the defense of the body in case of stress. Requirements of these amino acids may be increased in case of stress and in elderly people. Also, glutathione oral supplementation with whey protein has been shown to increase plasma GSH levels of HIV-infected patients (Eur. J. Clin. Invest. 2001; 31, 171-178).

Whey protein source, according to the present invention, may be unhydrolysed intact sweet whey, e.g., whey protein concentrate (WPC), whey protein isolate (WPI), or whey protein micelles (WPM) and whey protein hydrolysates (WPH) or a combination thereof. In one embodiment, the whey protein source may be a combination of whey protein concentrate and whey protein hydrolysates or whey protein isolates. In one embodiment, the composition of the present invention may be composed of at least about 60%-100% unhydrolysed intact whey protein, preferably, all or major part of the protein content is composed of 100% unhydrolysed intact whey protein.

In the present compositions, the whey protein source offer numerous health and nutritional advantages. It helps athletes in gain lean muscle mass and provides weight gain of patients suffering from chronic diarrhea and malabsorption of nutrients (cachexia). See G. Bounous et al., Clinical & Investigative Med., 16 (3):204-209 (June 1993). On the other hand, whey protein as WPC or WPI can also be used to lose weight, if combined with a low-calorie diet.

The positive impact of whey protein source on the immune system is widely recognized. WPC and WPI can enhance the immune system by virtue of the presence of certain "whey protein fractions," including serum albumin and the immunoglobulins, which have immunomodulating effects. Immunomodulating effects refer to those actions that keep the immune system at homeostasis—i.e., neither activating nor suppressing it beyond that which is beneficial to the body as a whole. The four major proteins in whey protein concentrates or isolates include, in order of prevalence, as follows: β-lactoglobulin, α-lactalbumin, bovine serum albumin (BSA), and the immunoglobulins in their entirety (including all five classes), each of which is known to be an important part of the immune system. C. V. Morr and E. Y. Ha, Crit. Rev. in Food Sci. Nutri., 33 (6):431-476 (1993).

WPC and WPI also contain a number of so-called "minor" whey protein factors that may have important non-nutritional properties. C. V. Mon and E. Y. Ha, supra; P. F. Fox, Developments in Dairy Chemistry, Fox, P. F., ed., Elsevier Applied Science, New York (1989). These "minor" whey protein factors include lactoferrin, lactophorin, lacto-peroxidase, and lysozyme, which are also understood to have antibacterial and other biological functions. B. Reiter, Int. J. Tissue React., 1:87 (1983); B. Reiter, Developments in Dairy Chemistry, 281, Fox, P. F., ed., Elsevier Applied Science, New York (1985); C. Kanno, J. Dairy Sc., 72:883 (1989).

Aside from the "major" and "minor" proteins, WPC also contains a variety of beneficial nutritional components, including ash, non-protein N compounds (nitrogen-containing compounds), lipids, lactose, phospholipids, as well as trace amounts of sodium, potassium, calcium, magnesium, and phosphorus. C. V. Morr, and E. A. Foegeding, Food Technol., 44:100 (1990). Nonprotein N compounds include products of protein catabolism that are ultimately converted to urea and excreted, such as blood urea nitrogen (BUN)— the form of urea that is transported through the bloodstream to the kidney for excretion. Thus, whey protein contains a host of proteinaceous components and other constituents, including vitamins and minerals that are known to be of critical nutritional importance in humans and animals.

Of the whey proteins discusses hereinabove, α-lactalbumin typically constitutes about 40% by weight of the total human milk proteins. In contrast, α-lactalbumin is present only in cow's milk at only 4-5% by weight of the total proteins. α-La has a high content of the amino acid, tryptophan, a precursor of the vitamin niacin. Thus, because of its tryptophan content, α-La is an excellent source of niacin equivalents. One niacin equivalent is defined as 1 milligram of niacin or 60 milligrams of tryptophan. Niacin functions as part of a coenzyme essential for metabolism including fat synthesis, tissue respiration and utilization of carbohydrate. It promotes healthy skin, nerves and digestive tract, aids in digestion and fosters a normal appetite. It has been reported that pH adjustment of whey to a more acid level during processing would cause a change in protein conformation, which, in turn, lead to a higher retention of α-La. See U.S. Pat. No. 6,312,755 B1.

The term "milk protein hydrolysate" refers to milk proteins that have been subjected to any type of hydrolysis. Thus, such milk protein hydrolysate may even include intact proteins that escaped hydrolysis and also any fractions of proteins obtained by the treatment of the hydrolysis.

The terms "sweet whey" and "acid whey" are also considered to be possible milk protein hydrolysates, because these materials are the product of enzymatic or acid hydrolysis of milk proteins. When skimmed milk is treated with enzymes or acids, sweet or acid whey, respectively, is separated in the absence of clotted casein. Sweet or acid whey then comprises whey protein hydrolysates and also minor proteins, which remain intact. Sweet or acid whey can be condensed, dried, fermented, delactosed, deminerlaized and deproteinated.

Whey, however, as is well known in the art, can also comprise intact proteins as well as different fractions of hydrolysed proteins.

U.S. Pat. No. 7,240,320 ("the '320 patent"), assigned to Nestec, S. A., and its European counterpart, European Patent No. 1314361 B1 ("the EP '361 patent"), describes a composition and method of preparing the composition, which provides a nutritionally-complete, calorically dense formula suitable for use as a ready-to use liquid composition. The composition contains a high concentration of whey protein of about 20-90 g/L, wherein at least 60% of the proteins are whey proteins. It is shelf-stable for up to 6 months or more at ambient temperature. However, with respect to the process of preparing the neutral whey composition, both '320 and EP '361 patents describe a two-step sterilization procedure using an indirect UHT (ultra high temperature) treatment. In comparison, the present invention offers an improved process of producing a neutral, shelf-stable and enteral non-gel liquid composition that employs a single-step sterilization approach and produces a higher amount of whey protein, ranging from about 8 g/100 g to about 13 g/100 g or from at least about 90 g/L to about 143 g/L and an energy content range from at least about 110 kcal/100 g to about 200 kcal/100 g. A single step sterilization approach, as in the present invention, is simpler and more cost-effective.

European Patent No. 0852468 B1 ("the EP '468 patent"), as well as its corresponding International Application No. PCT/US96/14052 (published as WO97/011614 A1) and U.S. Pat. No. 5,641,531, describe a liquid nutritional supplement having a pH of about 2.8-3.4, which is lower from that of the present invention (pH 3.5-4.3). The nutritional supplement is a clear liquid and possesses a thin texture and a highly-acceptable mouth feel. It is devoid of added fat and macronutrients. It also describes a specific process for making such supplements that contain up to 10% whey protein by weight and having a caloric density of at least 1.0 kcal/ml (between 1.20-1.25 kcal/ml). In contrast, the shelf-stable, acid whey compositions, according to the present invention, has energy content that ranges from at least about 100 kcal/100 g to about 260 kcal/100 g. The whey protein source is solely from whey protein isolates and not as a combination of other whey protein sources as used in the present invention. As described in the EP '468 patent, acid is added to the aqueous solution of whey protein isolate for pH adjustment prior to the addition of the carbohydrate portion. The inventors considered this step as being critical because they have discovered that "acidification of a protein/carbohydrate blend results in a finished product which has unacceptably high viscosity and a cloudy appearance." See the EP '468 Patent, at column 6, paragraph [0032]. This critical step, however, is not a concern for the present invention for producing the shelf-stable, acid whey liquid composition since the protein source is admixed with the carbohydrate source prior to the adjustment of the resulting second mixture.

Various approaches of preparing and using the whey protein micelles of the present invention are described in International Publication Nos. WO 2007/110411 A2, WO 2007/110421 A2, WO 2007/110422 A2, WO 2007/110423 A2, the disclosures of which are expressly incorporated herein by reference thereto.

With respect to the protein content in the compositions of the present invention, it may be at least about 8 g/100 g to at least about 13.5 g/100 g, wherein the total protein content is composed 60-100% whey. For example, the total protein content may compose of at least about 60%, 65%, 70%, 75%, 80%, 85%, 90%, 95% or 100% whey protein. Preferably, the total protein content may range from at least about 80-100%; 85-100%, 90%-100% or at least about 95%-100% whey protein. More preferably, the total protein content may compose of at least about 95%, 96%, 97%, 98%, 99% or 100% whey protein.

The whey protein may either be in form of unhydrolysed or hydrolysed intact whey protein. The protein content may be at least about 8 g/100 g; 8.5 g/100 g; 9 g/100 g; 9.5 g/100 g; 10 g/100 g; 10.5 g/100 g; 11 g/100 g; 11.5 g/100 g; 12 g/100 g; 12.5 g/100 g; 13 g/100 g; or 13.5 g/100 g of whey protein source, either in form of whey protein concentrate; whey protein isolates, whey protein micelles and whey protein hydrolysates or in any combination thereof.

For the process of the invention, whey proteins may be present in an amount of from at least about 8 to 13 g/100 g or from at least about 90 to 143 g/L for neutral, shelf-stable, and enteral non-gel liquid compositions; at least about 9 to at least about 13.5 g/100 g for shelf-stable, acid whey compositions having an energy content ranging from at least about 100¬264 kcal/100 g; and at least about 10 g/100 g for acid whey compositions having an energy content ranging from at least about 100-264 kcal/100 g and with 0% fat content.

The nutritional compositions of the present invention provide an energy content at the range of at least about 100 to 200 kcal/100 g, preferably at least about 185 kcal/100 g, for the shelf-stable, acid whey formulation having a total protein of at least about 13.5 g/100 g and a WPI/WPH ratio ranging from at least about of 50:50 to 80:20, preferably at least about 70:30. In another embodiment, the present invention provides an energy content at the range of at least about 200 to 260 kcal/100 g, preferably 245 kcal/100 g, for the shelf-stable, acid whey liquid formulation having a total protein of at least above 10 g/100 g and a WPI/WPH ratio ranging from at least about of 50/50 to 70/30, preferably at least about 60:40.

With respect to the neutral, shelf-stable and enteral non-gel liquid compositions, according to the present invention, the protein content may compose of 100% WPC or 100% WPM.

The total energy intake provided by the protein content in the shelf-stable, acid or neutral whey compositions may range from at least about 14-36%; at least about 20-54%; or at least about 15-40%.

Preferably, at least one carbohydrate source may be in the range of at least about 15 g/100 g to about 51 g/100 g; about 10-20 g/100 g; about 12-26 g/100 g; or about 16-30 g/100 g. The nutritional compositions includes at least one carbohydrate source, which provides at least about 39-46%; about 45-64%; about 60-85% or about 40-70% of the total energy intake of the nutritional composition. For example, a carbohydrate source may provide at least about 40% of the energy of the nutritional composition. Several carbohydrate sources may be used, which include maltodextrin, corn syrup, corn starch, modified starch, sucrose, lactose, fructose, oligofructose and mixtures thereof.

Also preferably, at least one lipid or fat source may be in the range of at least about 0.1 to 10 g/100 g; about 0-12 g/100 g or about 4-10 g/100 g, preferably at least about 0.2 to about 7 g/100 g. For shelf-stable, acid whey liquid composition having an energy content of at least about 245 kcal/100 g or a at least bout 264 kcal/100 g, the fat source is at least about 12 g/100 g of the total fat of the composition, which provides at least about 41% of the total energy of the nutritional composition. For example, a lipid source may provide about 30% of the total energy of the nutritional composition. The lipid source may be an oil from a vegetable, a dairy or an animal source or a combination thereof. Suitable lipid sources include high oleic sunflower oil, high oleic safflower oil, sunflower oil, safflower oil, rapeseed oil, soy oil, olive oil, canola oil, peanut oil, rice bran oil, butter fat, hazelnut oil, coconut oil, borage oil, black currant oil, evening primrose oil, flaxseed oil and structured lipids. The lipid source may include medium chain triglycerides (MCT), which is enriched with monounsaturated fatty acids (MUFAs) and polyunsaturated acids (PUFAs).

The compositions of the present invention may provide an energy content ranging from at least about 100 kcal/100 g to at least about 264 kcal/100 g for shelf-stable acid whey compositions.

For example, for shelf-stable, acid whey compositions having a whey protein content of at least about 13.5 g/100 g, these compositions may provide an energy content ranging from at least about 100 kcal/100 g to 264 kcal/100 g. For example, at least about 100-120, 120-130, 130-140, 140-150, 150-160, 160-180, 180-200, 200-220, 220-240, 240-264 kcal/100 g, preferably at least about 185 kcal/100 g or at least about 260 kcal/100 g. The ratio of whey protein micelles or whey protein concentrate or whey protein isolates to whey protein hydrolysates in the composition may range from at least about 40:60 to 100:0; 40:60 to 60:40; 50:50 to 80:20, preferably at a ratio of at least about 70:30.

For shelf-stable, acid whey compositions that have a whey protein content of at least about 9 g/100 g, these compositions may provide an energy content ranging from at least about 100 kcal/100 g to 264 kcal/100 g. For example, at least about 100-120, 120-130, 130-140, 140-150, 150-160, 160-180, 180-200, 200-220, 220-240, 240-264 kcal/100 g, preferably at least about 185 kcal/100 g or at least about 260 kcal/100 g. The ratio of whey protein isolates or whey protein concentrate or whey protein micelles to whey protein hydrolysates in such compositions may also range from at least about 40:60 to 100:0; 40:60 to 60:40; 50:50 to 80:20, preferably at a ratio of at least about 70:30.

For shelf-stable, acid whey composition having protein content of at least about 10 g/100 g, these compositions may provide an energy content that ranges from at least about 100 kcal/100 g to about 260 kcal/100 g, for example, at least about 100-120, 120-130, 130-140, 140-150, 150-160, 160-180, 180-200, 200-220, 220-240, 240-264 kcal/100 g. In addition, the ratio of whey protein isolates to whey protein hydrolysates in such compositions may range from at least about 40:60 to 100:0; 40:60 to 60:40; 50:50 to 80:20, preferably at a ratio of at least about 70:30.

For neutral, shelf-stable and enteral non-gel liquid compositions according to the present invention, these compositions may have an energy content ranging from at least about 110 kcal/100 g to about 200 kcal/100 g. For example, at least about 110-120 kcal/100 g, 110-130 kcal/100 g, 110-140 kcal/100 g, 120-140 kcal/100 g, 140-160 kcal/100 g, 160-180 kcal/100 g, or 180-200 kcal/100 g or at least above 140 kcal/100 g, preferably an energy content ranging from at least about 140 to 160 kcal/100 g. In one embodiment, the neutral, shelf-stable and enteral non-gel liquid composition may have an energy content that is at least above 140 kcal/100 g.

Prior to heating the whey protein aqueous solution, the pH is generally adjusted by either the addition of an acid or alkaline solution, which is preferably food grade. An example of an acid is hydrochloric acid, phosphoric acid, acetic acid, malic acid, citric acid, gluconic acid, lactic acid, adipic acid, tartaric acid, fumaric acid, carbonic acid, glucono-delta-lactone acid, ascorbic acid or mixtures thereof. An example of an alkaline solution includes sodium hydroxide, potassium hydroxide, or ammonium hydroxide.

The whey protein micelle concentrate (from evaporation or microfiltration) can be used in liquid form as a dispersion or in semi-solid form, or in a dried form. It may be used in a great variety of applications such as those described above with respect to the whey protein micelles applications.

An emulsifier, as used in the present invention, may include diglycerides, monoglycerides, lactic acid monoglyceride, glycerol monostearate, sodium stearoyl lactylates, and mixtures thereof.

A coloring agent may be a natural or an artificial coloring agent may include a fruit juice, a vegetable juices, riboflavin, a carotenoid, a tumeric, a lycopenes, an FD&C dye and an FD&C lake or combination thereof.

A sweetener may be selected from the group consisting of sucrose, fructose, glucose, and mixtures thereof. A sweetener may also be a none or low calorie sweetener.

The U.S. Recommended Daily Intake (USRDI) for vitamins and minerals are defined and set forth in the Recommended Daily Dietary Allowance-Food and Nutrition Board, National Academy of Sciences-National Research Council. Non-limiting examples of such vitamins and minerals include potassium, calcium, magnesium, iron, zinc, copper, manganese, chromium, molybdenum, selenium, phosphorous, iodine, beta-carotene, choline, vitamin A, vitamin C, iodine, vitamin B1, vitamin B2, vitamin B3, vitamin B5, vitamin B6, vitamin B7, vitamin B9, vitamin B12, vitamin D, vitamin E, and vitamin K.

As used herein, the term amino acid refers to amino acids in free form or pharmaceutically or nutritionally acceptable salt form. For example, essential amino acids include isoleucine, leucine, lysine, methionine, phenylalanine, threonine, tryptophane, valine, or histidine. Conditionally essential amino acids in free form or pharmaceutically or nutritionally acceptable salt include tyrosine, cysteine, arginine, or glutamine.

As used herein the term "soluble fiber" refers to soluble fibers such as agar, alginates, carubin, pectin, e.g. pectins from fruits and vegetables, e.g. from citrus fruits and apples, and its derivatives, beta-glucan, such as oat beta-glucan, carrageenans, in particular kappa, lambda and iota carrageenans, furcellaran, inulin, arabinogalactan, cellulose and its derivatives, scleroglucan, *psyllium*, such as *psyllium* seed husk, mucilages and gums, e.g. commonly available vegetable gums and more particularly konjac gum, xanthan gum, guar gum (guaran gum), locust bean gum, tara bean gum, gum tragacanth, arabic gum, karaya gum, gum ghatti, gellan gum and other related sterculia gum, alfalfa, clover, fenugreek, tamarind flour. Native and modified, e.g. hydrolyzed, soluble fibers may be used.

As used herein, the term "prebiotic" refers to a non-digestible food ingredient that stimulates the growth and/or activity of probiotics. Prebiotics of the present invention may include acacia gum, alpha glucan, arabinogalactans, beta glucan, dextrans, fructooligosaccharides, galactooligosaccharides, galactomannans, gentiooligosaccharides, glucooligosaccharides, guar gum, inulin, isomaltooligosaccharides, lactosucrose, lactulose, levan, maltodextrins, partially hydrolyzed guar gum, pecticoligosaccharides, retrograded starch, soyoligosaccharides, sugar alcohols, xylooligosaccharides, or a combination thereof.

As used herein the term "antioxidant" is preferably understood to include any one or more of various substances (as beta-carotene (a vitamin A precursor), vitamin C, vitamin E, and selenium) that inhibit oxidation or reactions promoted by Reactive Oxygen Species (ROS) and other radical and non-radical species. Additionally, antioxidants are molecules capable of slowing or preventing the oxidation of other molecules. As used herein, non-limiting examples of antioxidants include carotenoids, coenzyme Q10 ("CoQ10"), flavonoids, glutathione Goji (Wolfberry), hesperidine, Lactowolfberry, lignan, lutein, lycopene, polyphenols, selenium, vitamin A, vitamin B1, vitamin B6, vitamin B12, vitamin C, vitamin D, vitamin E, and combinations thereof. An embodiment of the present invention includes antioxidants.

As used herein, "complete nutrition" are preferably nutritional products that contain sufficient types and levels of macronutrients (protein, fats and carbohydrates) and micronutrients to be sufficient to be a sole source of nutrition for the animal to which it is being administered to. An embodiment of the present invention is intended to be a complete nutrition composition.

As used herein, "effective amount" is preferably an amount that prevents a deficiency, treats a disease or medical condition in an individual or, more generally, reduces symptoms, manages progression of the diseases or provides a nutritional, physiological, or medical benefit to the individual. A treatment can be patient- or doctor-related. In addition, while the terms "individual" and "patient" are often used herein to refer to a human, the invention is not so limited. Accordingly, the terms "individual" and "patient" refer to any animal, mammal or human having or at risk for a medical condition that can benefit from the treatment.

As used herein, "elderly" is preferably a human that is sixty-five years of age or older, more preferably 75 years or age or older.

As used herein, "incomplete nutrition" are preferably nutritional products that do not contain sufficient levels of macronutrients (protein, fats and carbohydrates) or micronutrients to be sufficient to be a sole source of nutrition for the animal to which it is being administered to. An embodiment of the present invention is intended to be an incomplete nutrition composition.

As used herein, "Long term administrations" are preferably continuous administrations for more than 6 weeks. An embodiment of the present invention is intended for long-term administration.

Composition is preferably understood to further include any number of additional ingredients, including, for example one or more, vitamin, mineral, sugar, a pharmaceutically acceptable carrier, excipient, flavor agent, or colorants.

As used herein, "Obesity" is preferably a condition in which the natural energy reserve, stored in the fatty tissue of animals, in particular humans and other mammals, is increased to a point where there is increase in adiposity and it is associated with certain health conditions or increased mortality. "Obese" is defined for an adult human as having a BMI greater than 30.

All dosage ranges contained within this application are intended to include all numbers, whole or fractions, contained within the range.

As used herein, "Short term administrations" are preferably continuous administrations for less than 6 weeks. An embodiment of the present invention is intended for short-term administration.

As used herein, the terms "treatment", "treat" and "to alleviate" is preferably to both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The terms "treatment" and "treat" also refer to the maintenance and/or promotion of health in an individual not suffering from a disease but who may be susceptible to the development of an unhealthy condition, such as nitrogen imbalance or muscle loss. The terms "treatment", "treat" and "to alleviate" are also intended to include the potentiation or otherwise enhancement of one or more primary prophylactic or therapeutic measure. The terms "treatment", "treat" and "to alleviate" are further intended to include the dietary management of a disease or condition or the dietary management for prophylaxis or prevention a disease or condition As used herein, a "tube feed" is preferably a complete or incomplete nutritional products that are administered to an animal's gastrointestinal system, other than through oral administration, including but not limited to a nasogastric tube, orogastric tube, gastric tube, jejunostomy tube (J-tube), percutaneous endoscopic gastrostomy (PEG), port, such as a chest wall port that provides access to the stomach, jejunum and other suitable access ports. An embodiment of the present invention is intended for tube-feed administration.

As used herein the term "vitamin" is preferably understood to include any of various fat-soluble or water-soluble organic substances (non-limiting examples include vitamin A, vitamin B1, vitamin B6, vitamin B12, vitamin C, vitamin D, vitamin E) essential in minute amounts for normal growth and activity of the body and obtained naturally from plant and animal foods or synthetically made, pro-vitamins, derivatives, analogs.

As used herein, Probiotics micro-organisms (hereinafter "probiotics") are preferably microorganisms (alive, including semi-viable or weakened, and/or non-replicating), metabolites, microbial cell preparations or components of microbial cells that could confer health benefits on the host when administered in adequate amounts, more specifically, that beneficially affect a host by improving its intestinal microbial balance, leading to effects on the health or well-being of the host. (Salminen S, Ouwehand A. Benno Y. et al "Probiotics: how should they be defined" Trends Food Sci. Technol. 1999:10 107-10). In general, it is believed that these micro-organisms inhibit or influence the growth and/or metabolism of pathogenic bacteria in the intestinal tract. The probiotics may also activate the immune function of the host. For this reason, there have been many different approaches to include probiotics into food products. Examples of probiotics are *Bifidobacterium* and *Lactobacillus* strains, such as *Bifidobacterium lactis* (German Culture Collection: DSM20215), a *Bifidobacterium longum* (CNCM 1-2170), *Lactobacillus paracasei* (CNCM 1-2116, CNCM 1-1292), *Lactobacillus johnsonii* (CNCM 1-1225), *Lactobacillus salivarius*, and further include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or a combination thereof.

The compositions of the present invention may be used as a combination in form of a pharmaceutical or nutritional composition. Preferably, nutritional compositions may be used. Compositions in accordance with the present invention may be employed for administration in any appropriate manner, e.g., enterally or orally, preferably in liquid form. Optionally, the compositions may be administered in the form of a tube feeding solution.

Optionally, the compositions according to the invention may be nutritionally complete, i.e. may include vitamins, minerals, trace elements as well as additional nitrogen, carbohydrate and additional fatty acid sources so that they may be used as the sole source of nutrition supplying essentially all the required daily amounts of vitamins, minerals, carbohydrates, fatty acids, proteins and the like. Accordingly, the compositions of the invention may be provided in the form of a nutritionally balanced complete meal, e.g. suited for oral or tube feeding. Preferably the compositions of the invention are for oral administration.

EXAMPLES

The following Examples illustrate certain preferred embodiments of the invention for the purpose of illustrating the process disclosed herein and do not, in anyway, limit the scope of the invention. In these Examples, the parts and percentages are by weight unless stated otherwise.

Example 1

A Neutral Whey Liquid Non-Gel Composition Having High Whey Protein Content From Whey Protein Concentrate (At Least About 10 g/100 g Or 110 g/l)

A shelf-stable, neutral whey liquid non-gel composition having up to 100% whey protein content (up to 10 g/100 g or 11 g/100 ml) was prepared following the flow diagram of FIG. 1.

The pH range of the resulting neutral whey liquid composition is about 6.8 to about 7.2. Other properties of the neutral whey liquid composition include low viscosity, pleasant sweet taste and shelf-stability for up to 9 months.

| | |
|---|---|
| Energy (kcal/100 g) | 155 |
| Total proteins (g/100 g) | 9.5 |
| % Whey in Total Proteins | 100 |
| Total Fat (g/100 g) | 6.5 |
| Total Carbohydrates (g/100 g) | 15 |
| Calcium (mg/100 g) | About 56 |
| Magnesium (mg/100 g) | About 25 |
| pH (–) | 7.0 |
| Viscosity at 20° C., 200 s$^{-1}$ (mPa · s) | About 40 |

To achieve the desired neutral whey liquid compositions of the present invention without any protein perceivable aggregation (gelling), several conditional parameters were applied, as illustrated in FIG. 1. The dissolution of all ingredients (emulsifiers, whey protein concentrate, maltodextrin, sugar, oils, minerals, and vitamins) was made in water at a temperature between 30° C. and 60° C. The pH of the mix was then adjusted to at least about 6.5 to 7.5, preferably between 6.8 to 7.2, with KOH or citric acid. The heat treatment operation comprises two sequential steps: (1) preheating at 60-80° C. for less than 15 seconds using an indirect heat treatment; and (2) sterilization at 140-145° C. for 7 seconds using Direct Steam Injection. The sterilized phase was then cooled down to 20° C.-30° C. and aseptically filled in sterile bottles.

Example 2

A Neutral Whey Liquid Non-Gel Composition Having High Whey Protein Content From Whey Protein Micelles (At Least About 13 g/100 g Or 143 g/l)

Figure 2:
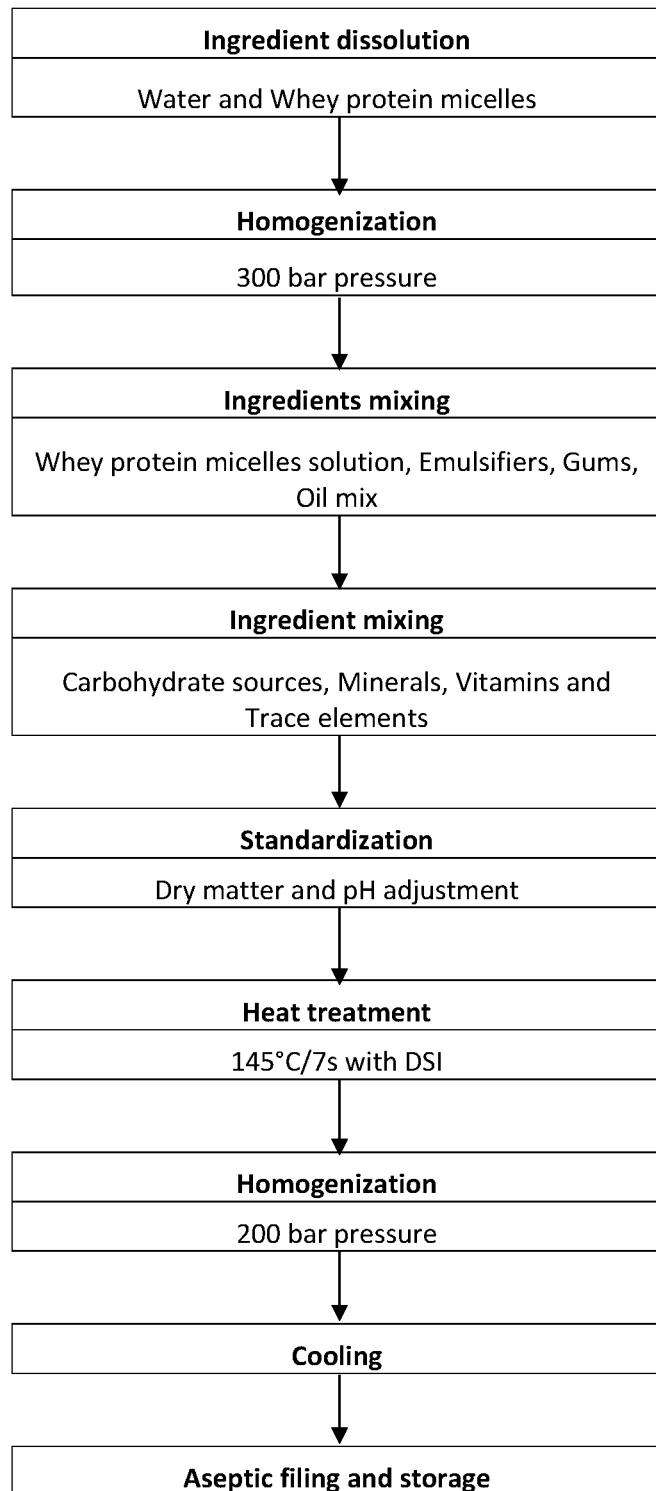
FIG. 2 is a flow diagram of how a shelf-stable, neutral whey liquid non-gel composition having up to 100% whey protein content (at least 13 g/100 g or 143 g/100 ml) was prepared.

A shelf-stable, neutral whey liquid non-gel composition having up to 100% whey protein content (at least about 13 g/100 g or 143 g/100 ml) was prepared following the flow diagram in FIG. 2.

The pH range of the resulting neutral whey liquid composition is about 6.8 to about 7.2. Other properties of the neutral whey liquid composition include low viscosity, pleasant sweet taste and shelf-stability.

| | |
|---|---|
| Energy (kcal/100 g) | 150 |
| Total proteins (g/100 g) | 13 |
| % Whey in Total Proteins | 100 |
| Total Fat (g/100 g) | 6 |
| Total Carbohydrates (g/100 g) | 11.5 |
| pH (–) | 7.0 |
| Viscosity at 20° C., 200 s$^{-1}$ (mPa · s) | About 80 |

To achieve the desired neutral whey liquid composition of the present invention without any protein perceivable aggregation (gelling), conditional parameters similar to example 1 were applied, as illustrated in FIG. 2.

Example 3

An Acid Whey Liquid Composition Having A Low Energy Content of At Least About 100 To 185 kcal/100 g, A Total Protein Content of At Least About 13.5 g/100 g And A Ratio of Whey Isolate:Whey Hydrolysate of At Least About 70:30

| INGREDIENTS Ingredient Name | Ingredient Mass Kg |
|---|---|
| Glucose Syrup | 9.00 |
| Whey Protein Isolate | 10.67 |
| Sugar | 9.00 |
| Phosphoric Acid | 0.106 |
| Vegetable Oil | 7.00 |
| Whey Protein Hydrolysate | 5.64 |
| Emulsifier | 0.20 |
| Total Ingredients | 41.61 |
| Water to be added | 58.39 |
| Total Finished Product | 100.00 |

The macronutrients breakdown of the acid whey liquid composition having a low energy content and a total protein content of at least about 13.5 g/100 g are as follows:

| Kcal/100 g | | g/100 g product | |
|---|---|---|---|
| Energy | Fat | Protein | Carbohydrate |
| 185 | 7 | 13.5 | 16.5 |

Figure 3:
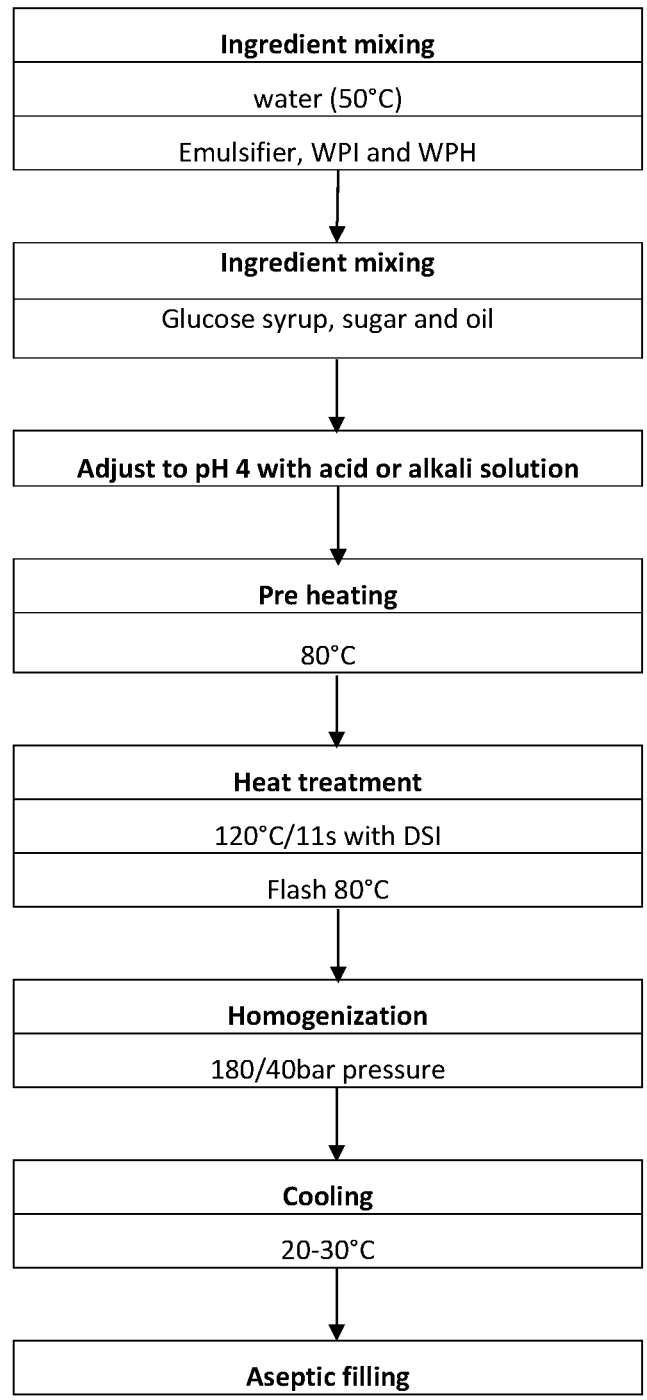
FIG. 3 is a flow diagram for formulating an acid whey liquid compositing having a low energy content.

FIG. 3 illustrates a process for formulating the above-mentioned acid whey liquid composition having a low energy content of at least about 100 to 185 kcal/100 g, a total protein content of at least about 13.5 g/100 g and a ratio of whey isolate:whey hydrolysate of at least about 70:30:

Example 4

An Acid Whey Liquid Composition Having A "High" Energy Content of 245 kcal/100 g, A Total Protein Content of 10 g/100 g And A Ratio of Whey Isolate:Whey Hydrolysate of 60:40

| INGREDIENTS Ingredient Name | Ingred. Mass kg |
|---|---|
| Whey Protein Isolate | 7.20 |
| Glucose Syrup | 41.25 |
| Fructose | 17.00 |
| Na Citrate | 0.41 |
| NaCl | 0.30 |
| Phosphoric Acid | 0.58 |
| Whey Protein Hydrolysate | 5.64 |
| Emulsifier | 0.20 |
| Potassium Citrate | 0.06 |
| Aroma | 0.09 |
| Total Ingredients | 72.63 |
| Water to be added | 27.37 |
| Total Finished Product | 100.00 |

The macronutrients breakdown of the acid whey liquid composition having a high energy content and a total protein content of 10 g/100 g are as follows:

| Kcal/100 g | | g/100 g product | |
|---|---|---|---|
| Energy | Fat | Protein | Carbohydrate |
| 245 | 0.2 | 10 | 51 |

Figure 4:
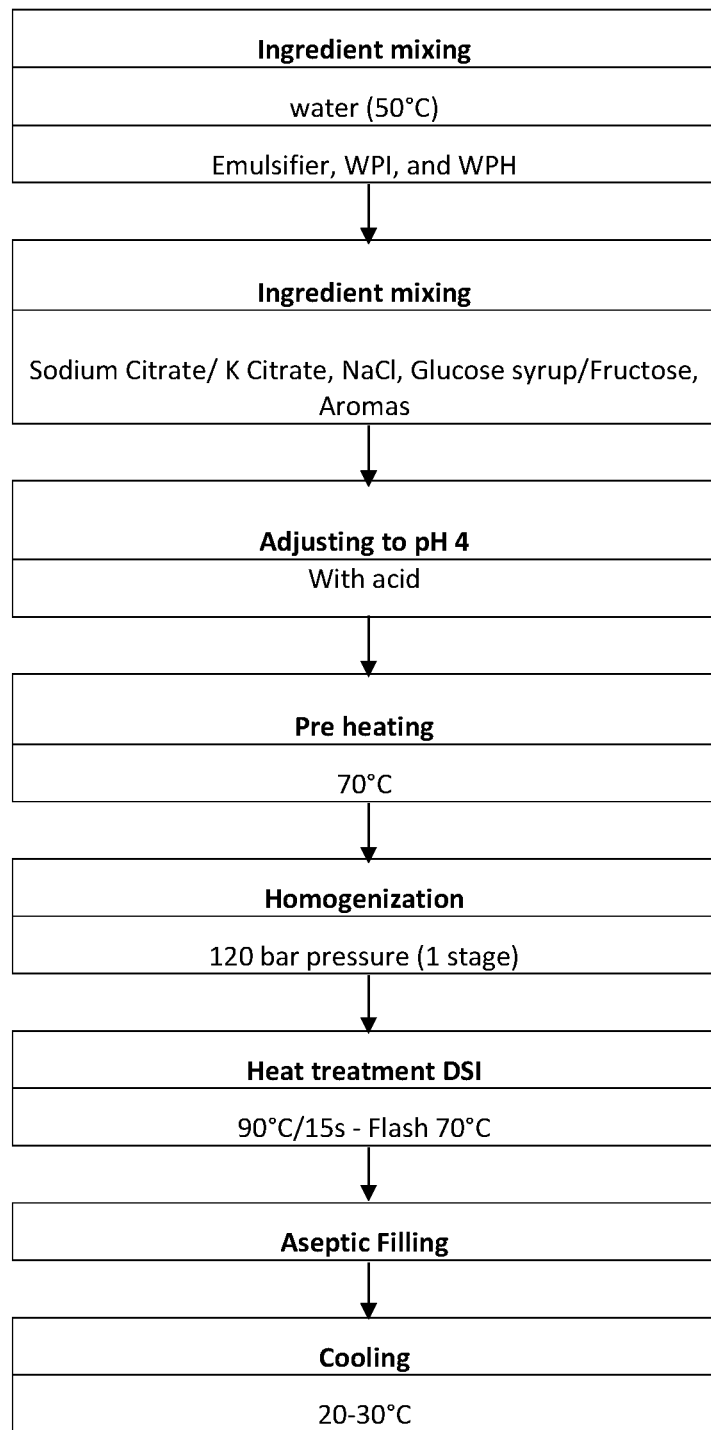
FIG. 4 is a flow diagram for formulating an acid whey liquid composition having a high energy content.

FIG. 4 illustrates a process for formulating the above-mentioned acid whey liquid composition having a "high" energy content of 245 kcal/100 g, a total protein content of at least about 10 g/100 g and a ratio of whey isolate:whey hydrolysate of at least about 60:40:

In another embodiment, a whey composition in accordance with this application can be combined with and vitamin D, preferably 1, 25 Dihydroxy vitamin D or preferably 25 hydroxy vitamin D. This combination is especially helpful for: Improves muscular-skeletal health in elderly persons; helping to reduce the decline in muscular skeletal health in elderly persons; improving mobility in elderly persons; helping to regain/restore muscular-skeletal functionality in elderly persons after illness or injury; and helping to improve bone mass in elderly persons.

The term "about," as used herein, should generally be understood to refer to both numbers in a range of numerals. Moreover, all numerical ranges herein should be understood to include each whole integer within the range.

It is to be understood that the invention is not to be limited to the exact configuration as illustrated and described herein. Accordingly, all expedient modifications readily attainable by one of ordinary skill in the art from the disclosure set forth herein, or by routine experimentation therefrom, are deemed to be within the spirit and scope of the invention as defined by the appended claims.

The invention claimed is:

1. A method for producing a neutral, shelf-stable non-gel liquid composition for enteral administration, the method comprising:
    admixing at least one whey protein source with at least one carbohydrate source, lipid source, and emulsifier in water at a temperature range of between 30° C.-60° C. to form a first mixture;
    adding to the first mixture at least one ingredient selected from the group consisting of a mineral, a vitamin, a trace element, and a thickening agent, and at least one additional ingredient to form a second mixture;
    adjusting the pH of the second mixture to between 6.5 and 7.5 by adding a food grade base or acid to obtain a neutral, non-gel liquid composition that does not gel;
    preheating the neutral, non-gel liquid composition at a temperature of between 60° C.-80° C.;
    a single step of exposing the neutral, non-gel liquid composition under ultra-high temperature treatment using direct steam injection at a temperature range of between 140-145° C. for 7 seconds holding time to obtain the neutral, shelf-stable non-gel liquid composition;
    homogenizing the neutral, shelf-stable non-gel liquid composition at a temperature range of 60° C.-80° C. at a total pressure of 200 bars;
    cooling the neutral, shelf-stable non-gel liquid composition at a temperature range of 20° C.-35° C.; and
    transferring the neutral, shelf-stable non-gel liquid composition into a sterilized container for enteral use,
    the neutral, shelf-stable non-gel liquid composition having a total protein content ranging from 8 g/100 g to 13 g/100 g based on the total weight of the neutral, shelf-stable non-gel liquid composition, and the total protein content is 100% unhydrolyzed intact whey protein,
    a content of the at least one carbohydrate source ranging from 10 g/100 g to 20 g/100 g based on the total weight of the neutral, shelf-stable non-gel liquid composition, and the at least one carbohydrate source is selected from the group consisting of maltodextrin, sucrose, and lactose,
    a content of the at least one lipid source ranging from 4 g/100 g to 10 g/100 g based on the total weight of the neutral, shelf-stable non-gel liquid composition, and the at least one lipid source is selected from the group consisting of corn oil, rapeseed oil, and soybean oil, and
    the neutral, shelf-stable non-gel liquid composition having a pH ranging from 6.5 to 7.5 and an energy content of at least 140 kcal/100 g based on the total weight of the neutral, shelf-stable non-gel liquid composition.

2. The method of claim 1, wherein the admixing step is performed at a temperature of 30° C.-35° C.

3. The method of claim 1, wherein the thickening agent comprises starch.

4. The method of claim 1, wherein the food grade base is selected from the group consisting of potassium hydroxide and sodium hydroxide.

5. The method of claim 1, wherein the food grade acid is selected from the group consisting of citric acid and phosphoric acid.

6. The method of claim 1, wherein the preheating is conducted at 65° C. or less by a tubular heat exchanger.

7. The method of claim 1, wherein the direct steam injection is followed by a flash at a temperature range of between 60° C.-80° C. or at 65° C.

8. The method of claim 1, wherein the homogenizing step is performed at 65° C.

9. The method of claim 1, wherein the at least one whey protein source is selected from the group consisting of whey protein concentrate, whey protein micelles.

10. The method of claim 1, wherein the at least one whey protein source is whey protein micelles.

11. The method of claim 1, wherein the energy content of the neutral, shelf-stable non-gel liquid composition ranges from about 180 kcal/100 g to 200 kcal/100 g.

* * * * *